(12) United States Patent
King et al.

(10) Patent No.: US 7,943,804 B2
(45) Date of Patent: May 17, 2011

(54) LUTEIN EXTRACTION FROM OZONE-TREATED PLANT SOURCES

(75) Inventors: Joan M. King, Baton Rouge, LA (US); Yu Wang, Natick, MA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 12/279,913

(22) PCT Filed: Feb. 20, 2007

(86) PCT No.: PCT/US2007/062404
§ 371 (c)(1),
(2), (4) Date: Mar. 27, 2009

(87) PCT Pub. No.: WO2007/098435
PCT Pub. Date: Aug. 30, 2007

(65) Prior Publication Data
US 2010/0240933 A1 Sep. 23, 2010

Related U.S. Application Data

(60) Provisional application No. 60/775,480, filed on Feb. 21, 2006.

(51) Int. Cl.
*C07C 35/21* (2006.01)
(52) U.S. Cl. .................................................. 568/816
(58) Field of Classification Search ................... None
See application file for complete search history.

(56) References Cited

U.S. PATENT DOCUMENTS

| 6,169,217 B1 | 1/2001 | Cheryan ........................ 568/816 |
| 6,329,557 B1 | 12/2001 | Rodriguez et al. ............ 568/834 |
| 6,737,552 B1 | 5/2004 | Crombie ........................ 568/816 |

OTHER PUBLICATIONS

Antony, J.I.X. et al., "Lutein," The World of Food Ingredients, Apr./May, pp. 64-67 (2001).
Bewley, J. D.; Black, M. Structure of seeds and their food reserves. In Physiology and Biochemistry of Seeds in Relation to Germination, vol. 1 Development, Germination and Growth; Spinger-Verlag: Berlin, 1978; Chapter 2, pp. 7-37.
Dollear, F.G. et al., "Elimination of aflatoxins from peanut meal," J. Am. Oil Chem. Soc., vol. 45, pp. 862-865 (1968).
Dwarakanath, C.T. et al.,, "Reduction of aflatoxin levels in cottonseed and peanut meals by ozonization," J. Am. Oil Chem. Soc., vol. 45, pp. 93-95, (1968).
Food and Agricultural Organization (FAO), 1998. World corn production. FAOSt database, Food and Agricultural Organization, Rome, Italy.
Gonzalez de Mejia, E., M. et al., "Antimutagenic activity of natural xanthophylls against Aflatoxin B1 in *Salnonella typhimurium*," Environmental and Molecular Mutagenic, vol. 30, pp. 346-353 (1997).

Gonzalez de Mejia, G. et al., "Antimutagenicity of xanthophylls present in Aztec Marigold (*Tagetes erecta*) against 1-nitropyrene," Mutation Res., vol. 389, pp. 219-226 (1997).
Huck, C.W. et al., "Development and evaluation of a new method for the determination of the carotenoid content in selected vegetables by HPLC and HPLC-MS-MS," J. Chromatogr. Sci., vol. 38, pp. 441-449 (2000).
Johnson, E.J. , "The role of carotenoids in human health," Nutrition in Clinical Care, vol. 5, pp. 56-65 (2002).
Lakshminarayana R. et al., "Determination of major carotenoids in a few Indian leafy vegetables by high-performance liquid chromatography," J Agric Food Chem, vol. 53, No. 8, pp. 2838-2842 (2005).
Li, H.-B et al., "Isolation and purification of lutein from the microalga *Chlorella vulgaris* by extraction after saponification," J. Agric. Food Chem., vol. 50, pp. 1070-1072 (2002).
Maron, D.M. et al., "Revised methods for the Salmonella mutagenicity test," Mutation Res., vol. 113, pp. 173-215 (1983).
McKenzie, K.S., "Degradation and detoxification of common chemical contaminants of food ad water using ozone generated by electrolysis," A Ph.D. Dissertation , Texas A&M University. p. 200 (1997).
McKenzie, K.S. et al., "Aflatoxicosis in turkey poults is prevented by treatment of naturally contaminated corn with ozone generated by electrolysis," Poultry Science, vol. 77, pp. 1094-1102 (1998).
Moros, E.E. et al., "Analysis of Xanthophylls in Corn by HPLC," J. Argic. Food. Chem, vol. 50, pp. 5787-5790 (2002).
"News: TAMU pilot plant to use acetone as solvent," Inform, vol. 12, pp. 730-731 (Jul. 2001).
Norton, R.A., "Effects of carotenoids on aflatoxins synthesis by *Aspergillus falvus*," Phytopathology, vol. 87, No. 8, pp. 815-821 (1997).
Park, K.Y. et al., "Antimutagenic activity of flavonoids from the heartwood of *Rhus verniciflua*," Journal of Ethnopharmacology, vol. 90, pp. 73-79 (2004).
Piedade, F.S. et al, "Distribution of aflatoxins in corn fractions visually segregated for defects," Brazilian Journal of Microbiology, vol. 33, pp. 250-254 (2002).
Prudente, A.D., Efficacy and Safety Evaluation of Ozonation to Degrade Aflatoxin in Corn. A Master Thesis, Louisiana State University, (2001).
Prudente, A.D. et al., "Efficacy and Safety Evaluation of Ozonation to Degrade Aflatoxin in Corn," Journal of Food Science, vol. 67, pp. 2866-2872 (2002).
Rauscher, R., R. et al., "In virto antimutagenic and in vivo anticlastogenic effects of carotenoids and solvent extracts from fruits and vegetables rich in carotenoids," Mutation Res., vol. 413, pp. 129-142 (1998).

(Continued)

*Primary Examiner* — Brian J Davis
(74) *Attorney, Agent, or Firm* — Bonnie J. Davis; John H. Runnels

(57) ABSTRACT

The use of ozonation has been discovered to increase the lutein extraction from aflatoxin-free corn and for some batches of alfalfa. In addition, the ozonation will substantially decrease any aflatoxin in the plant source. The structure of lutein as indicated by HPLC elution profile and the function of lutein using an antimutagenic activity was shown not to be affected by the ozonation.

17 Claims, 9 Drawing Sheets

OTHER PUBLICATIONS

Rooney, L.W. et al., "Food uses of whole corn and dry-milled fractions,". In: Corn Chemistry and technology, Watson, S.A. et al. (Eds)., Am. Assoc. Cereal Chemists. St. Paul, MN. p. 399-429 (1987).

Samarajeewa, U. et al., "Detoxification of aflatoxins in foods and feeds by physical and chemical methods," J. Food Protect, vol. 53, No. 6, pp. 489-501 (1990).

Slattery, M.L. et al., "Diet and colon cancer: assessment of risk by fiber type and food source," J Natl Cancer Inst., vol. 80, No. 18, pp. 1474-1480 (1968).

Wang, Yu, "Evaluation of Lutein and Protein in Ozone Treated Corn," A thesis submitted to the Department of Food Science, Louisiana State University, Aug. 2005.

Wang, Y. et al., "Evaluation of Lutein and Protein in Ozone-Treated Corn," An abstract for the 2005 Annual Meeting of the Institute of Food Technologists, published online Mar. 2005.

LUTEIN EXTRACTION FROM OZONE-TREATED PLANT SOURCES

This is the United States national stage of international application PCT/US2007/062404, international filing date Feb. 20, 2007, which claims the benefit of the filing date of provisional application 60/775,480, filed Feb. 21, 2006, under 35 U.S.C. §119(e).

TECHNICAL FIELD

This invention pertains to method to enhance the extraction of lutein from plant sources, including but not limited to corn and alfalfa, using ozonation and a hexane extraction procedure. In addition, the ozonation was shown not to affect the antimutigenic activity of the lutein.

BACKGROUND ART

Lutein

Lutein and zeaxanthin are plant pigments, commonly called xanthophylls, which belong to the group of carotenoids. Lutein is chemically represented as dihydroxy carotenoid, $\beta$, e-carotene-3,3'-diol.

Structure of Lutein:

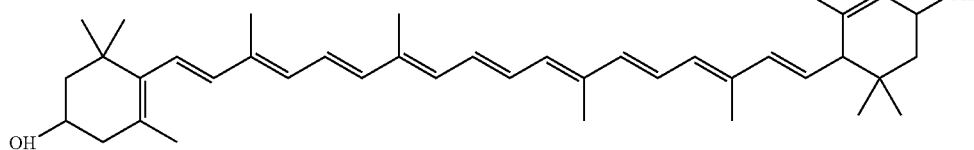

Because humans are not capable of synthesizing carotenoids in vivo, the presence of lutein in human tissue is solely dependent upon dietary origin. Lutein is found in green plants (e.g., alfalfa, wheat grass, barley grass, kale, spinach, broccoli, green beans, green peas, lima beans, cabbage, collards, mustard greens, and turnip greens), certain flowers (e.g., marigold flower petals), and certain yellow fruits and vegetables (e.g., carrots, peaches, mango, papaya, squash, and oranges). (Table 1; see also, U.S. Pat. No. 6,737,552) In corn, lutein is mostly found in the horny endosperm. Zeaxanthin is a structural isomer of lutein and is similar to lutein relative to food sources, human metabolism, and tissue storage. See E. J. Johnson, "The role of carotenoids in human health," Nutrition in Clinical Care, vol. 5, pp. 56-65 (2002). Both lutein and zeaxanthin are also called xanthophylls or macula pigments.

The major food sources of lutein are presented in Table 1 (Huck et al., 2000). Spinach, kale and broccoli have the highest amount of lutein. Data on the lutein content of foods frequently include zeaxanthin and are reported as lutein+zeaxanthin, making examination of specific effects of dietary lutein difficult. In terms of food sources, human metabolism, and tissue storage, lutein and zeaxanthin are similar.

TABLE 1

Food Sources of Lutein

| Food | Lutein Content (µg/100 g wet wt) |
|---|---|
| Broccoli | 2358 |
| Kale | 6390 |
| Carrot | 280 |
| Spinach | 3920 |
| Tomato granulate | 226 |
| Tomato powder | 39 |
| Tomato flakes | 99 |

Adapted from (Huck et al., 2000)

Sweet potato leaves are another source of lutein. In foods, lutein can be found either in its free form, bound to proteins, or esterified as a mono- or di-ester. Most lutein and zeaxanthin found in plant leaves are bound to proteins. Lutein and other xanthophylls have been extracted from corn using alcohols, i.e., ethanol and isopropanol, and by extraction after saponification. See U.S. Pat. No. 6,169,217; and H.-B. Li et al., "Isolation and purification of lutein from the microalga Chlorella vulgaris by extraction after saponification," J. Agric. Food Chem., vol. 50, pp. 1070-1072 (2002). Although acetone has been proposed as an alternative extraction solvent for cottonseed, it has not been suggested for other plants, and in fact, was found not to be a good extraction solvent for rice bran oil and saw palmetto. See "News: TAMU pilot plant to use acetone as solvent," Inform, vol. 12, pp. 730-731 (July 2001). Although marigold (Tagetes erecta) flowers are an excellent source of lutein, corn (Zea mays) has been identified as a more economical source of lutein because more value-added products, such as lutein, oil, and zein (known for its anti-microbial and anti-hypertensive activities), can be isolated from corn than marigold flowers.

An important characteristic of lutein and zeaxanthin is the presence of nine or more conjugated carbon-carbon double bonds, which allows susceptibility to light, oxygen, heat, and acid degradations. These conjugated double bonds have the ability to quench singlet oxygen with increasing activity depending on the number of conjugated double bonds. This unique structure of lutein and zeaxanthin allows them to function as primary antioxidants in biological systems by scavenging peroxyl radicals. Generally, carotenoids are believed to form resonance stabilized radical cations or radical adducts, which are not capable of participating in autoxidation reactions.

The presence of hydroxyl groups makes lutein and zeaxanthin noticeably more polar than their respective analogs of $\alpha$- and $\beta$-carotene. Lutein is soluble in both nonpolar and polar solvents as shown in Table 1. See J. I. X. Antony et al., "Lutein," The World of Food Ingredients, April/May, pp. 64-67 (2001).

TABLE 2

Lutein: Physical Properties and Solubility in Organic Solvents

A. Physical Properties of Lutein

| | |
|---|---|
| Molecular formula | $C_{40}H_{56}O_2$ |
| Molecular weight | 568.85 |
| Melting point | 183-190° C. |
| Appearance | Yellow prisms with metallic luster |
| Stability | Unstable to light and oxygen; Stable if stored at −20° C. under a nitrogen atmosphere |
| Solubility in water | Insoluble |

B. Solubility of Lutein in Organic Solvents

| Solvent | Solubility (mg/L) |
|---|---|
| Acetone | 800 |
| Acetonitrile | 100 |
| Benzene | 600 |
| Chloroform | 6000 |
| Cyclohexane | 50 |
| Cyclohexanone | 4000 |
| Dimethyl formamide | 1000 |
| Ethyl alcohol | 300 |
| Ethyl acetate | 800 |
| Ethyl ether | 2000 |
| Hexane | 20 |
| 2-Propanol | 400 |
| Methyl alcohol | 200 |
| Methyl tert butyl ether | 2000 |
| Tetrahydrofuran | 8000 |
| Toluene | 500 |

Adapted from Antony et al., 2001.

Some lutein is known to be bound as lutein ester, and potassium hydroxide has been shown through the process of saponification to free lutein from the lutein ester (Antony et al., 2001). There is also an indication that lutein is bound to protein in corn. When the content of total xanthophylls in whole corn was compared with that of corn gluten meal, total xanthophyll concentration was 145.91±2.06 µg/g corn gluten meal, which was about 7.2 times higher than that of whole corn assayed under similar conditions. The protein content of gluten meal is about 60% (dry basis) or about 7.9 times higher than protein content in whole corn (7.6%). It was also shown that if hexane was used to extract the oil from corn, about eighty five percent of the xanthophylls remained with the defatted corn. (Moros et al., 2002).

Lutein in Health and Disease

Dietary carotenoids are thought to provide health benefits in decreasing the risk of disease, particularly eye disease. Eating leafy vegetables, which are rich in lutein and zeaxanthin, have been suggested to decrease the risk for eye disease called Age-Related Macular Degeneration (AMD). AMD is a degenerative condition of the region of the retina that is responsible for central vision, and is the most common cause of irreversible vision loss among older people. The carotenoids in the eye are concentrated in the inner retinal layer of the macula. Evidence from human studies suggest that dietary intake of carotenoids can lead to their accumulation in the retina and, therefore may provide protection against retinal degeneration. Lutein can also be useful in the prevention of other angiogenic diseases such as breast and colon cancer. See U.S. Pat. No. 6,329,557.

An inverse relationship between lutein intake and colon cancer has been reported, finding that a person who consumed more lutein-containing foods had a lower risk of colon cancer. The study followed 1,993 subjects diagnosed with colon cancer, and compared them with a control group of 2,410 who did not have colon cancer (Slattery et al., 1988). The participants were asked to report the foods they had eaten during a time period two years before or two years prior to their diagnosis. The nutrients contained in the foods were then calculated. Of all the carotenoids investigated, only lutein and zeaxanthin showed a protective effect against colon cancer. The antioxidant effect of lutein and zeaxanthin is linked to their biochemical effectiveness as scavengers of oxygen radicals, as well as their reaction with cell membranes in the colon, which are susceptible to carcinogenesis.

Antimutagenicity of Lutein

Xanthophylls are excellent antioxidants with antimutagenic and anticarcinogenic properties. Pure lutein and xanthophylls from Aztec Marigold flower (*Tagetes erecta*) have been shown to inhibit the mutagenicity of AFB1, using test based on *Salmonella* strains. (Gonzalez de Mejia et al., 1997). The study indicated that lutein can inhibit AFB1 mutagenicity by forming a complex between lutein and AFB1, therefore limiting the bioavailability of AFB1. In addition, lutein was shown to inhibit the mutagenicity of 1-nitropyrene (1-NP) and benzo[a]pyrene and 2-amino-3-methylimidazo[4,5-f]quinoline (Rauscher et al., 1998).

Corn Production and Ozonation

Corn (*Zea mays*) is a popular and widely consumed food and feed commodity in many communities throughout the world. Corn susceptibility to aflatoxin contamination, however, provides a potential health hazard to both human consumers and animals. See F. S. Piedade et al., "Distribution of aflatoxins in corn fractions visually segregated for defects," Brazilian Journal of Microbiology, vol. 33, pp. 250-254 (2002). Corn is of great importance because of its oil, starch, and protein content. Some batches of alfalfa are also known to contain aflatoxin.

Corn is currently the third most planted field crop after wheat and rice. The bulk of corn production occurs in the United States, Peoples Republic of China, and Brazil, which together account for 73% of the annual global production of 589.4 million tons (FAO, 1998). In most warm and humid regions the corn crop is highly susceptible to fungal invasion and aflatoxin production. Current estimates show that in 1998, 25% of corn fields in Louisiana were rejected or never harvested due to suspected aflatoxin contamination. Moreover, the presence of aflatoxins in food and feeds poses serious problems in human and animal health. Aflatoxin B1 is the most potent of four naturally occurring aflatoxins and has been the focus of considerable research. (McKenzie, 1997).

To limit human exposure to aflatoxins, several types of decontamination processes exist, including physical, chemical and biological methods. Currently, chemical methods are the most practical approaches to rid corn of inactive aflatoxins. Ozone treatment is one method that has been used successfully. Ozone, a powerful oxidizing agent, reacts across the 8,9-double bond of the furan ring (Samarajeewa et al., 1990). Ozone has been shown to reduce aflatoxin in cottonseed meal and peanut meal (Dollear et al., 1968; Dwarakanath et al., 1968). Aflatoxins in corn are reported reduced by 92-95% after being treated with 200 mg/min ozone for 92 hours (McKenzie, 1997; Prudente and King, 2002).

Research has been done to evaluate the effects of ozone gas in reducing aflatoxin concentration in aflatoxin-contaminated agricultural products. It was reported that ozone (25 mg/min) reduced aflatoxins in cottonseed meal and peanut meal. (Dwarakanath et al., 1968) In cottonseed meal, 91% of the total aflatoxin was destroyed and decreased from 214 to 20 ppb after 2 hr of ozonation. In peanut meal, 78% of aflatoxin was destroyed from 82 to 18 ppb after 1 hr. In 1997, corn spiked with aflatoxins and naturally contaminated rice powder was treated with ozone. (McKenzie et al., 1998) A rapid degradation of AFB1 and AFG1 was reported using 2 wt. % ozone, while AFB2 and AFG2 were more resistant to oxidation and needed higher levels of ozone. In a similar study, aflatoxins were reduced by 95% in samples treated with 14 wt % ozone for 92 hours at a flow rate of 200 mg/min. (McKenzie et al., 1998; Prudente and King, 2002) Turkey poults fed with ozone-treated contaminated corn did not show harmful effects as compared to turkey poults fed with untreated contaminated corn (McKenzie et al., 1998).

Corn is a rich source of flavonoids, polyphenols and carotenoids (Rooney and Serna-Saldivar, 1987). The occurrence of these antioxidants reduces aflatoxin levels in the grains (Norton, 1997). Flavonoids, carotenoid and polyphenols are known to mitigate the toxic and or mutagenic effects of aflatoxin (Park et al., 2004; Gonzalez de Mejia et al., 1997). Pure α-carotene and lutein, both of which occur in corn, reduced the mutagenic effect of aflatoxin to 2% that of control (Gonzalez de Mejia et al., 1997).

U.S. Pat. No. 7,109,361 discusses a method to extract lutein from plant material using a series of solvent extractions specific for oleoresin obtained from alfalfa or other leafy green plants.

U.S. Pat. Nos. 6,909,021 and 6,737,552 discusses a method to extract lutein from green plant materials using supercritical fluid extraction procedures, where the supercritical fluid may include $CO_2$, $CH_2CH_2$, $CH_3CH_3$, and $N_2O$.

U.S. Pat. No. 6,824,645 discusses use of ozone to oxidize cellulose-containing fibrous material prior to production of paper or nonwoven products.

U.S. Pat. No. 6,129,217 discusses the extraction of lutein from corn using an alcohol for lutein extraction, preferably ethanol. Hexane is used to separate out corn oil, prior to the alcohol extraction of lutein.

U.S. Pat. Nos. 6,120,822 and 6,171,625 discuss the decontamination of agricultural products contaminated with mycotoxins (including aflatoxin) using ozonation.

U.S. Pat. No. 5,602,286 discusses extraction of xanthophylls from corn gluten using alcohol and saponification.

U.S. Pat. No. 5,457,190 discusses the use of ozone to remove color from aliphatic glycosides prepared using a fatty alcohol and a hydrous saccharide source, including COM syrup.

Although ozonation has been proven to be an effective method for decontamination of aflatoxin in corn, its effect as an oxidizing agent on the structure and function of other beneficial corn products has not been evaluated. In particular, the effect of ozonation on the structure of lutein has not been evaluated. Moreover, because of the beneficial use of lutein, there is a need for additional methods to more effectively extract lutein from plant sources.

DISCLOSURE OF INVENTION

We have discovered a new method to enhance the extraction of lutein from plant sources, involving the use of ozonation of the plant source, followed by lutein extraction using an appropriate solvent. Lutein and protein content in ozonated corn, both clean and contaminated with aflatoxin, was determined. The lutein extracted using hexane from clean ozone-treated corn was about 28.36 µg/g, which was higher than the amount extracted from non-ozonated clean corn (22.75 µg/g). However, the presence of aflatoxin reversed the ozonation effect. Lutein extracted using hexane from aflatoxin-contaminated, ozonated corn was 11.69 µg/g, which was lower than the amount extracted from non-ozonated, contaminated corn (16.42 µg/g). Even though the ozonation significantly reduced the aflatoxin, the total amount of lutein extracted after ozonation was less than the untreated lutein extraction. In both contaminated and uncontaminated corn samples, the protein content of the ozone-treated corn was lower than that of untreated corn, indicating that some of the protein might be destroyed or made unavailable the ozonation process. The extracted corn lutein was shown to have a similar structure as determined by elution on a HPLC system and was shown to retain the ability to inhibit aflatoxin B1 mutagenicity, using *Salmonella typhimurium* tester strains TA-100 tester strain. The corn-extracted lutein was more effective at inhibiting AFB1 mutagenicity than a lutein standard at similar concentrations. In a similar system, alfalfa was ozonated before the extraction of lutein. In alfalfa, ozonation for a period of time of 12 hr or greater degraded the lutein. However, at 1 hr ozonation, the lutein was not degraded, and the amount of lutein extracted was increased by about 7% in one batch of alfalfa. The lutein extracted from alfalfa was shown to vary with different batches.

MODES FOR CARRYING OUT THE INVENTION

Example 1

Materials and Methods

Figure 1:
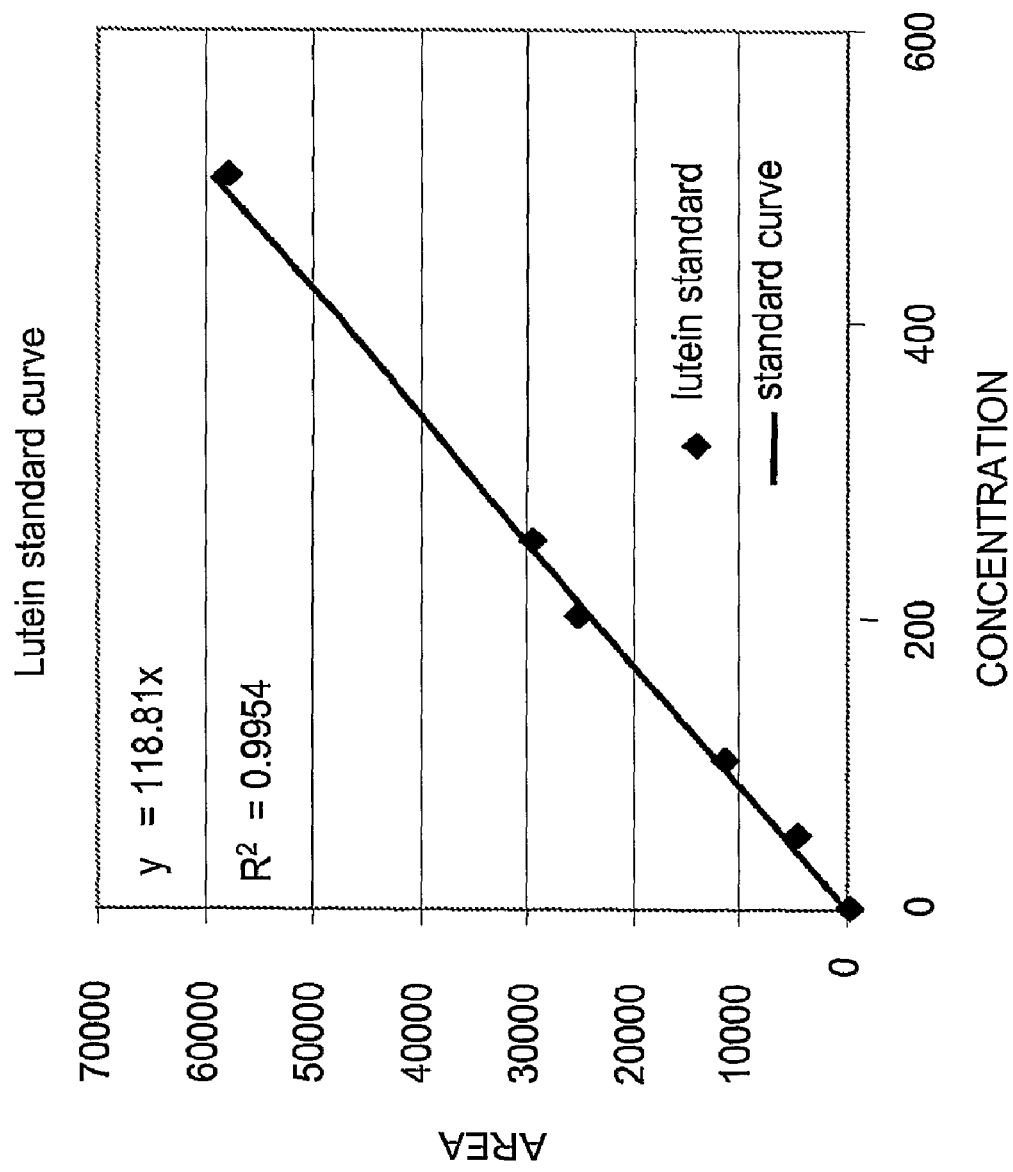
FIG. 1 illustrates the lutein standard curve generated from HPLC (high performance liquid chromatography) chromatograms using different concentrations of lutein and measuring the area under the curve.

Chemicals. Ethanol, potassium hydroxide, hexane, acetone (HPLC grade), petroleum ether, and methanol (HPLC grade) were obtained from Fisher (Fairlawn, N.J.). Ampicillin, D-biotin, magnesium sulphate, sodium ammonium phosphate, citric acid monohydrate, L-histidine, tetracycline, magnesium chloride, sodium dihydrogen phosphate, disodium hydrogen phosphate, β-nicotinamide adenine dinucleotide phosphate (NADP, sodium salt), glucose-6-phosphate, glucose, sodium chloride, potassium chloride, lutein standard, pure aflatoxin standard and butylated hydroxy toluene (BHT) were purchased from Sigma Chemical Co. (St. Louis, Mo.). The BHT was used as an antioxidant. Other anti-oxidants that could be used include purple gallate, butylated hydroxyanisole (BHA), tert butyl hydroquinone (TBHQ), citric acid and α-tocopherol. Electrophoretic gels (4-12% Bis-Tris gels, catalog no. NP 0321), lithium dodecyl sulfate sample buffer (catalog no. NP 0007), molecular weight marker (catalog no. LC 5677), acetic acid, running buffer (catalog no. NP 0002), and staining solutions (catalog no. 46-016) were obtained from Invitrogen (Carlsbad, Calif.). Bacto agar was obtained from Difco Laboratories (Detroit, Mich.). Oxoid nutrient broth NO. 2 was bought from Unipath LTD (Basingstoke, Hampshire, England). Rat liver post-mitochondrial supernatant (S9 mix) was purchased from Molecular Toxicology Inc., (Boone, N.C.). The bacterial tester stain TA100 was kindly provided by University of California, Davis (Davis, Calif.).

Corn Sample. Corn Samples were kindly provided by Lynntech, Inc. (College Station, Tex.). The samples were treated with ozone at Lynntech, Inc. as follows: Ten kilograms each of corn sample with and without aflatoxin contamination was treated with ozone. For such treatment, the corn sample was placed into a 30-gallon polyethylene reactor with a false bottom. A 10-15 in. headspace was allowed to achieve even ozone dispersion throughout the corn. The reactor lid was fitted with ¼ in Teflon bulkheads. Ozone gas, 10-12 wt %, flowed in through the top at an approximate rate of 2 L/min. A 2.5 L/min vacuum was pulled at the bottom of the reactor. All corn samples were treated for a total of 96 hr with treatment occurring at 12-15 hr intervals and with mixing every 30 hr. For a control, untreated corn was similarly treated but without the ozone flow. The treatment protocol produced the following groups: untreated clean corn, ozone-treated clean corn, naturally contaminated corn, and ozone-treated naturally contaminated corn.

Sample Preparation. Ten kilograms (10 kg) of corn sample from each treatment group were initially ground using a Romer Hammer Mill, and then further ground using a Brinkmann mill such that the ground sample would pass through a No. 20 mesh sieve. The samples were then stored at 4° C. until further analysis.

Extraction of Lutein. Lutein extraction was a modification of the procedure described by Moros et al. (2002). Triplicate ground corn samples, 20 g of each treatment type, were individually placed in 500 ml Erlenmeyer flasks, and 120 ml 0.1% (w/v) BHT-EtOH solution was added to each flask. The flasks were sealed with screw caps and placed in a 75° C. water bath for 5 min. The flasks were removed from the water bath, and 4 ml 80% KOH was added to each flask for saponification. The flasks were then shaken for 2 min and returned to the water bath for 10 min. After the samples were saponified, the flasks were immediately placed into an ice bath to cool. Then 60 ml cold, deionized water was placed into each flask, followed by 30 ml hexane, and followed by shaking. The flasks were then centrifuged at 2500 rpm for 10 min. The top hexane layer was removed with a pipette and added to a separate 250 ml Erlenmeyer flask. This hexane extraction was repeated until the top hexane layer was colorless. All hexane extracts were combined in the same flask. The hexane extracts were then placed in a stream of nitrogen to evaporate the hexane until no liquid remained. The residue was solubilized in 5 ml HPLC mobile phase (methanol/acetone 90:10), and stored at −20° C. for later use in HPLC analysis and in the Ames test for mutagenic activity. An initial experiment used acetone for the extraction of lutein. Acetone was not as good a solvent as hexane in extracting lutein from the corn. It is believed that other non-polar solvents could be used in the extraction, including without limitation, benzene, cyclohexane, toluene, etc.

HPLC Analysis for Lutein Concentration. The analytical HPLC system consisted of a reversed phase Supelco (Bellefonte, Pa.) Discovery C18 column (id 3 mm×25 cm), a Waters 2690 separation module, a 996 photodiode array detector, and a Millennium chromatography manager. A guard column (4 mm×23 mm) containing the same packing materials as the C-18 column was installed ahead of the C18 column. The mobile phase was a mixture of methanol and acetone at a ratio of 90:10. The flow rate was 1.0 ml/min during the entire run. The injected volume of all samples was 20 μl. The detector was set at 456 nm. Each analysis was performed in triplicate. The concentration of lutein extracted from the corn was calculated by comparing the peak area with that of a standard lutein peak area.

Extraction of Protein from Corn. Corn flour (200 g) from the ground corn sample above was defatted by extraction with 500 ml petroleum ether at 21° C. overnight in a 1000 ml Erlenmeyer flask. The defatted flour was air-dried under a hood, extracted with stirring with 1000 mL 70% ethanol containing 0.5 M NaCl in water for 4 hr at 21° C., and refrigerated until equilibrated to 4° C. Then the mixture was centrifuged at 4000 rpm for 10 min at 4° C. The supernatant was decanted into a container, and the ethanol was removed under vacuum by rotary evaporation. The remaining protein solution was lyophilized, and the protein concentration in the powder was determined by nitrogen analysis (N×6.25) (2410 Nitrogen Analyzer, Perkin-Elmer, Shelton, Conn.). All protein assays for each treatment were done in triplicate.

Electrophoresis of Corn Protein Mixture. SDS-PAGE electrophoresis was conducted following the procedure from Invitrogen (Carlsbad, Calif.). Lyophilized corn protein extract powder, from above, at 1 mg/mL was dissolved in sample buffer. Ten microliters of the protein sample was added to 25 μL sample buffer and 65 μL deionized distilled water following instructions from the gel's manufacturer. Electrophoretic separation was conducted using a Mini-VE electrophoresis unit (Amersham Pharmacia Biotech, Piscataway, N.J.). The resulting gel was stained using Novex Colloidal Blue (Invitrogen, Life Technologies; Carlsbad, Calif.). Each sample was run in duplicate.

Evaluation of Antimutagenicity of Lutein. The antimutagenicity of lutein extracts was tested using the Ames test, a standard *Salmonella*/microsomal mutagenicity assay as described by Maron and Ames (1983). Working in a laminar flow hood, disinfected with 80% alcohol, a single colony was selected from an ampicillin master plate and placed in 40 ml of sterile nutrient broth in an Erlenmeyer flask. The flask was lightly capped to allow airflow and placed in a gyratory water bath, set at 200-250 rpm and 37° C., for 12-14 hr. In this test, the TA100 test strain was used. After incubation, growth was confirmed by measuring the turbidity using a spectrophotometer at 650 nm. Sterile Oxoid Broth No. 2 was used as a blank. Absorbance readings in the range of 0.75-0.85 A indicated an optimal cell density of $1-2\times10^9$ bacterial cells/ml.

Aroclor 1254-induced rat liver (S9) was used to enhance the bioactivation of the AFB1. The S9 suspension contains several microsomal enzymes which help transform the aflatoxin into the reactive metabolite. The S9 suspension was prepared just before commencement of the test. All apparati and solutions were sterilized, and all operations conducted under a laminar flow hood. Before preparing the S9 mix, the lutein extracts which had been dried in stream of nitrogen as described above were reconstituted in dimethyl sulfoxide (DMSO) and diluted (by a factor of 5, 25 and 625). A pure lutein standard was also solubilized in DMSO at various concentrations (0, 0.002, 0.02, 0.08, 2, and 10 µg/plate). The concentrations of aflatoxin B1 in DMSO used in each plate for the AFB1 standard were 10, 50, 100, 250, and 500 ng/plate. During the assay, the S9 mix was kept on ice. AFB1 (500 ng) was combined with 0.2 ml histidine/biotin solution, 0.1 ml TA100, 0.1 ml lutein standard or lutein extracts and 0.5 ml S9 mix with 2 ml soft top agar. The mixtures were vortexed, poured onto a minimal glucose agar plate, and incubated at 37° C. for 48 hr. The number of revertants for each treatment was counted, and was compared against natural revertants and against the AFB1 standard curve. All assays were done in triplicate.

Statistical Analysis. Each analysis of the control and treatment groups was replicated in triplicate. Student's t-test procedure (Excel Data Analysis, Microsoft Inc., Seattle, Wash.) was used to compare the levels of lutein in the treated and untreated corn. In the Ames test, the statistical significance of the differences between the lutein standard and lutein extract was determined using Student's t-test. The difference among means was considered significant at $p \leq 0.05$.

Example 2

Ozonation and Lutein Extraction From Corn

Figure 2:
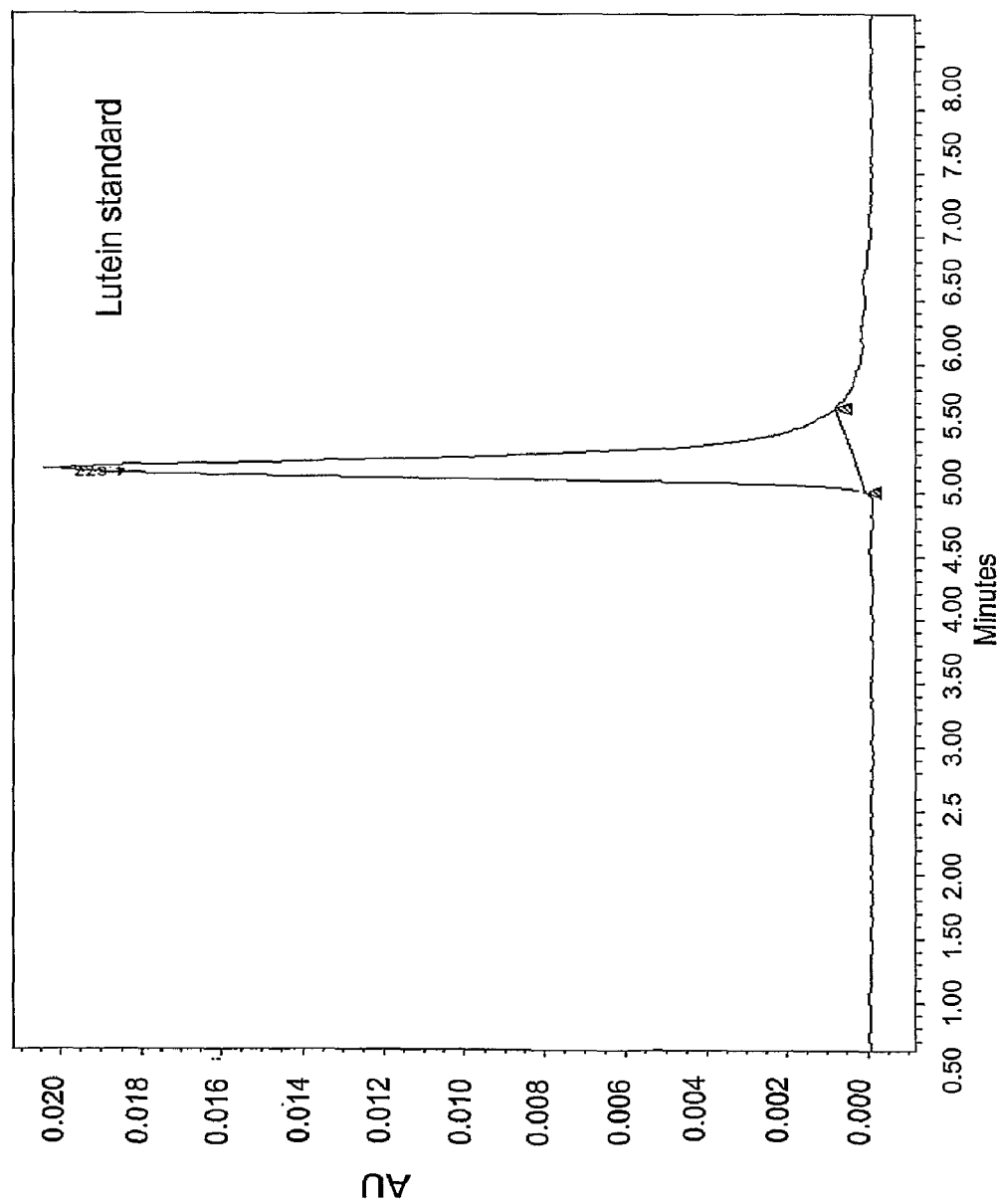
FIG. 2 illustrates a HPLC (high performance liquid chromatography) chromatogram showing the elution profile of a lutein standard, using HPLC conditions optimized to detect lutein.
Figure 3:
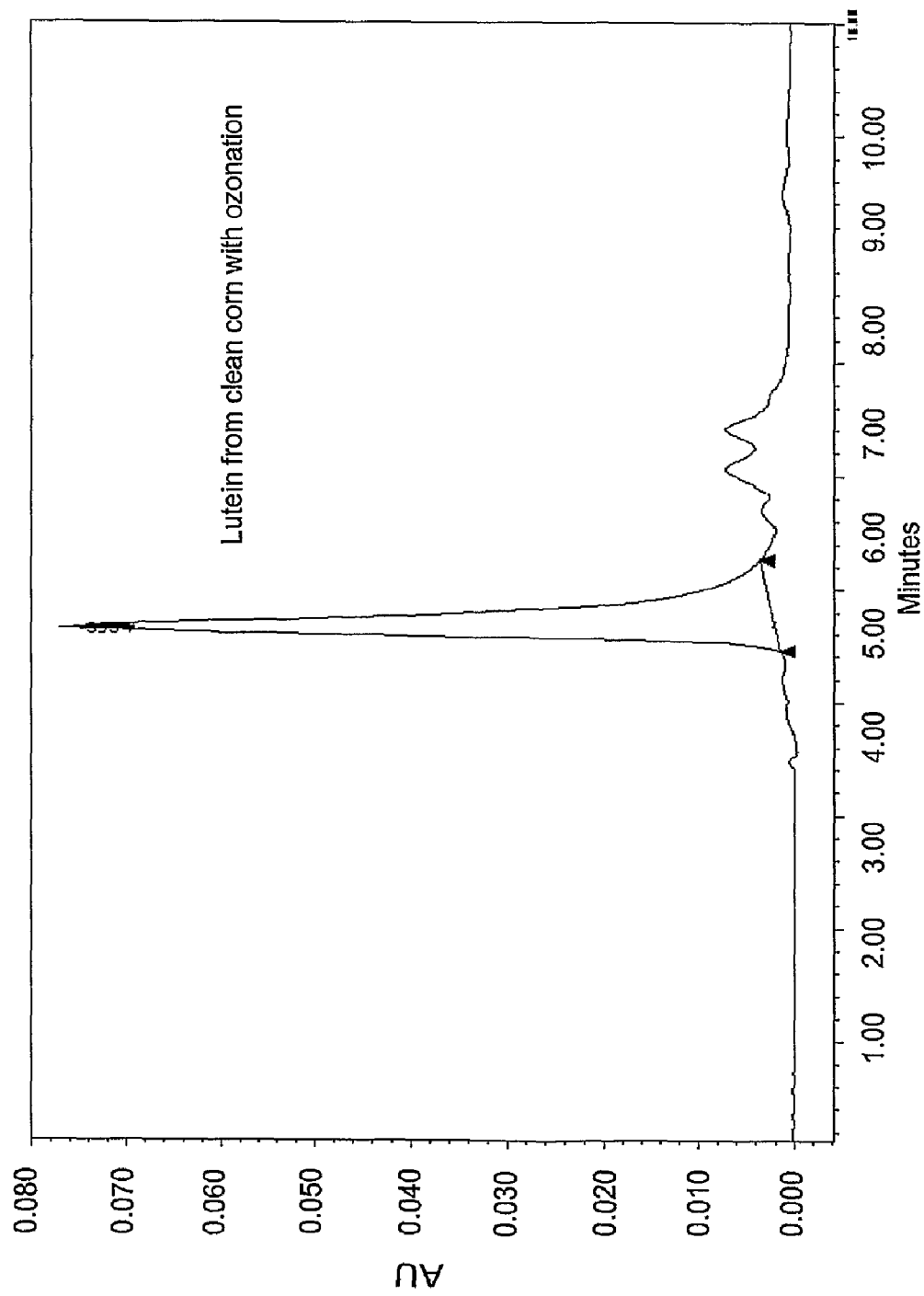
FIG. 3 illustrates a HPLC (high performance liquid chromatography) chromatogram showing the elution profile of the lutein extract from uncontaminated, ozonated corn, using HPLC conditions optimized to detect lutein.
Figure 4:
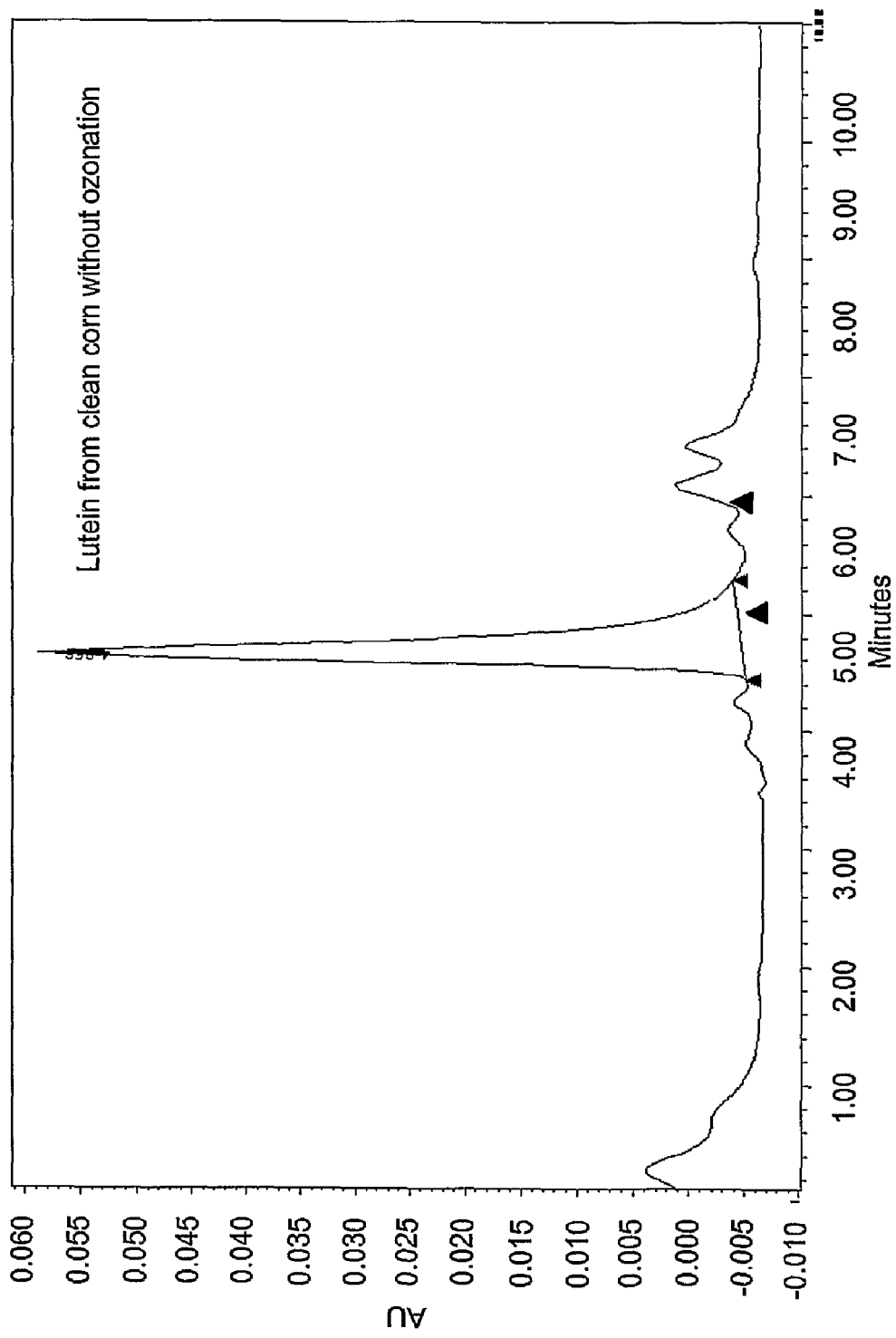
FIG. 4 illustrates a HPLC (high performance liquid chromatography) chromatogram showing the elution profile of the lutein extract from uncontaminated, non-ozonated corn, using HPLC conditions optimized to detect lutein.
Figure 5:
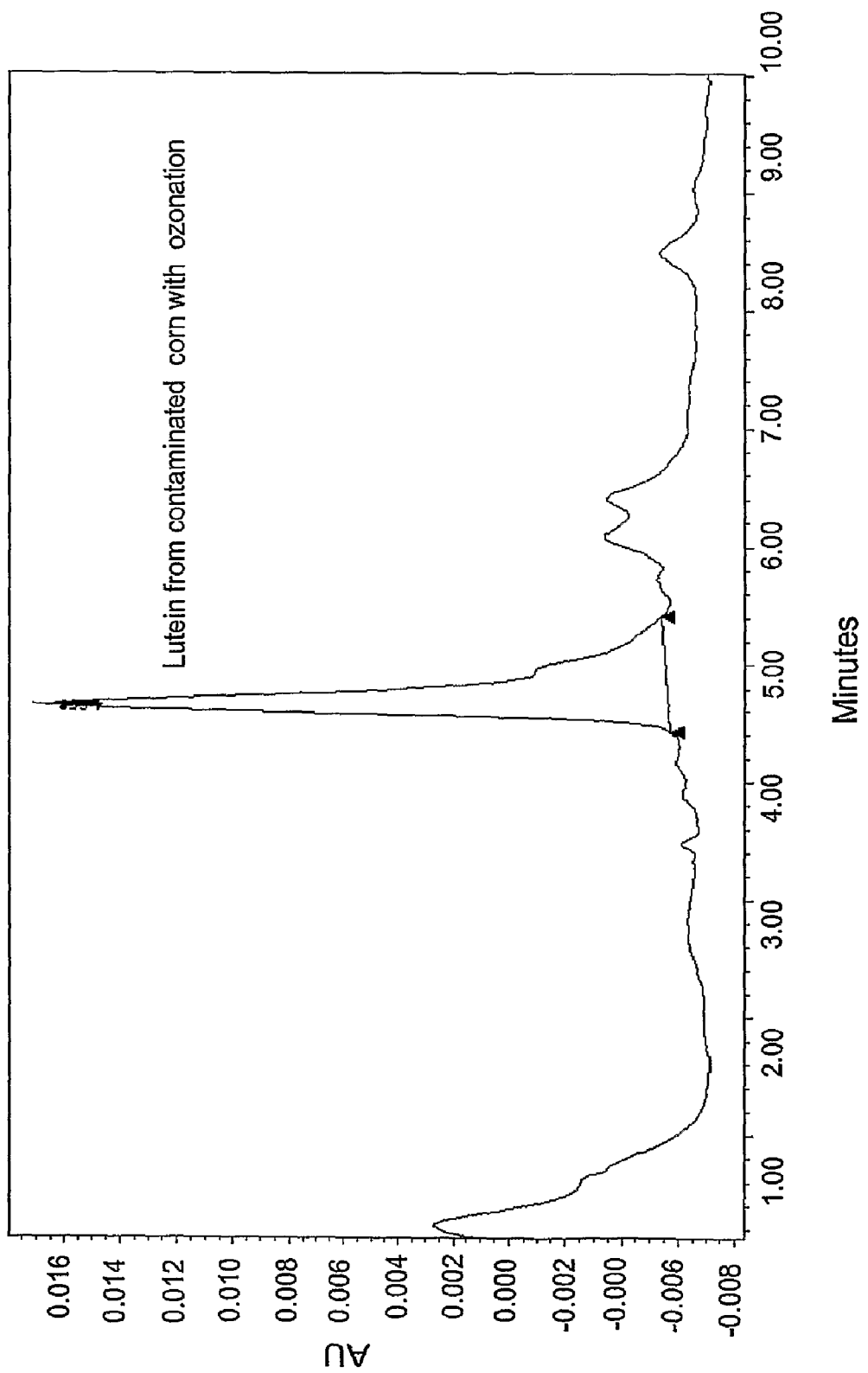
FIG. 5 illustrates a HPLC (high performance liquid chromatography) chromatogram showing the elution profile of the lutein extract from contaminated, ozonated corn, using HPLC conditions optimized to detect lutein.
Figure 6:
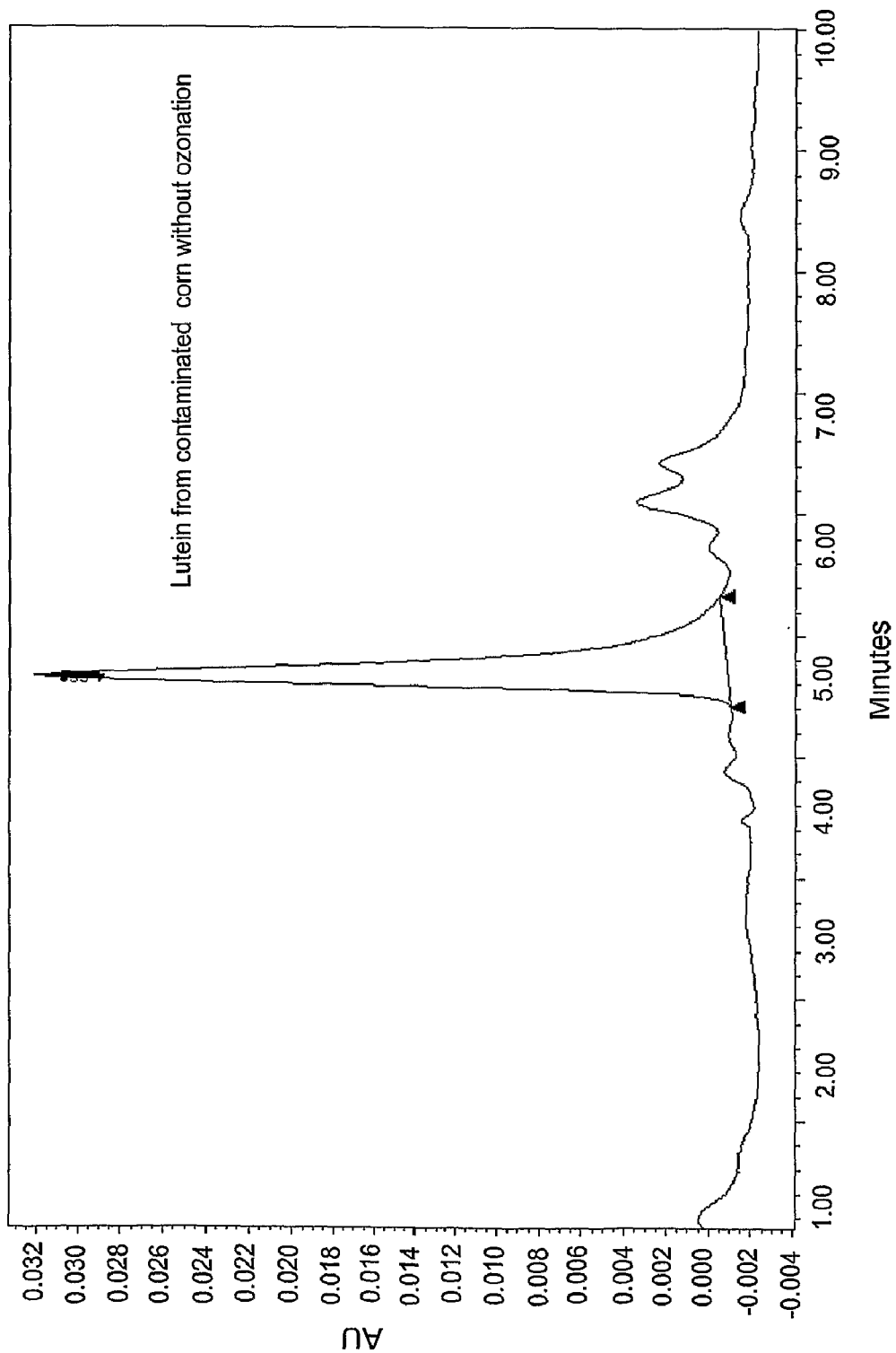
FIG. 6 illustrates a HPLC (high performance liquid chromatography) chromatogram showing the elution profile of the lutein extract from contaminated, non-ozonated corn, using HPLC conditions optimized to detect lutein.

A standard curve for determining lutein concentration was constructed by plotting HPLC peak absorbance area of the lutein peak (y axis) against a known injected concentration of lutein using a standard (x axis). As shown in FIG. 1, the equation of the best fit linear line was y=118.81x, with $R^2$=0.9954. A typical HPLC elution profile of lutein using the C18 column and reverse-phase chromatography is shown in FIG. 2. The retention time was about 4.6 min for lutein. The literature also reports that the retention time of lutein standard using the C18 column and a similar mobile phase was about 4.5 min. (Lakshminarayana et al., 2005; Li et al., 2002).

FIGS. 3, 4, 5 and 6 illustrate HLPL chromatograms of the lutein extract from clean corn with ozonation, clean corn without ozonation, contaminated corn with ozonation, and contaminated corn without ozonation, respectively. The lutein extracts were prepared using one BHT-EtOH extraction and three hexane washes as described in the methods above. The HPLC peaks were well separated by the C18 column. Identification of the lutein peak was based on the retention time and the spectra of absorbance maxima as compared to the lutein standard. Lutein samples were identified at a retention time of 4.6 min with absorbance maxima at 456 nm. According to the literature, the two, shorter peaks seen in FIGS. 3-6 that elute at a later time may be zeaxanthin and chlorophyll, respectively. (Moros et al., 2002; and Lakshminarayana et al., 2005) Specific analysis of zeaxanthin and chlorophyll standards was not done.

All the peaks of different corn samples eluted at a similar retention time and peak shape, but the area under the peak, a reflection of the lutein concentration in the sample, was different. Table 3 gives the content of lutein in the different corn samples.

TABLE 3

Lutein contents (µg/g) of different corns

| Sample | Lutein content (µg/g corn) |
|---|---|
| Clean corn with ozonation | 28.36 ± 0.35 |
| Clean corn without ozonation | 22.75 ± 0.11 |
| Contaminated corn with ozonation | 11.69 ± 0.12 |
| Contaminated corn without ozonation | 16.42 ± 0.19 |

As shown in Table 3, ozonation affected the total amount of lutein recovered from the corn when hexane was used to extract the lutein. The amount of extracted lutein in the clean corn increased from about 22.75 µg/g to about 28.36 µg/g, when treated with ozonation. The amount of extracted lutein in the contaminated corn actually decreased from about 16.42 µg/g to about 11.69 µg/g after treatment with ozonation. Thus the effect of ozonation on the amount of extracted lutein was reversed when the starting material was changed from clean corn to contaminated corn.

Statistical analysis indicated that the level of extracted lutein in the ozonated, clean corn was significantly higher than that in untreated clean corn ($P \leq 0.001$). In a similar manner, the level of extracted lutein in the ozonated, contaminated corn was significantly lower than that in untreated contaminated corn ($P \leq 0.001$).

The average amount of extracted lutein previously reported in corn was 14.68 µg/g, which was a little bit lower than the result of clean corn without ozonation. (Moros et al., 2002) However, when the extraction step was repeated five times in this report, the amount of xanthophylls increased to 22.81 µg/g. (Moros et al., 2002) In an earlier experiment, when acetone was used to extract lutein from the ozonated corn, the lutein extraction was less than was obtained with hexane, and the amount of extracted lutein was less in the ozonated samples than in the untreated samples. (Data not shown.) We believe that acetone is not a good solvent for extraction of lutein from the corn kernals.

Without wishing to be bound by this theory, it is believed one reason for the higher amount of extracted lutein in clean corn pretreated with ozone may be that some lutein is bound to or trapped by other compounds in the corn, such as fatty acids, protein and starch. Ozonation may release this lutein from those compounds, resulting in a higher extraction of lutein. Without wishing to be bound by this theory, it is believed that the lutein is bound to the zein protein in corn.

Example 3

Ozonation and Protein Extraction From Corn

The protein content in corn treated as above was also determined using the methods in Example 1. Table 4 indicates the content of protein in different corn samples.

TABLE 4

Protein content in the different corn samples

| Sample | Protein content (% by weight) |
|---|---|
| Clean corn with ozonation | 10.56% |
| Clean corn without ozonation | 12.16% |
| Contaminated corn with ozonation | 8.85% |
| Contaminated corn without ozonation | 12.04% |

As shown in Table 4, the amount of extracted protein in the ozone-treated corn was lower than that extracted from untreated corn for both clean and contaminated corn. In clean corn, the percent of protein was 10.56% of ozone-treated corn and 12.16% in the untreated corn. In contaminated corn, the percent of protein was 8.85% in ozone-treated corn and 12.04% in untreated corn. Thus, the effect of ozonation was to decrease the % protein in both clean and contaminated corn. It is known that corn contains about 70-75% starch, 5% lipids (triglycerides), and 11% protein by weight. (Bewley et al., 1978). The protein content of corn in our experiment is thus similar to that of the literature. Our results suggest that ozone can destroy the protein, and thus could be another avenue for lutein release from protein in ozonated-treated, clean corn.

Figure 7:
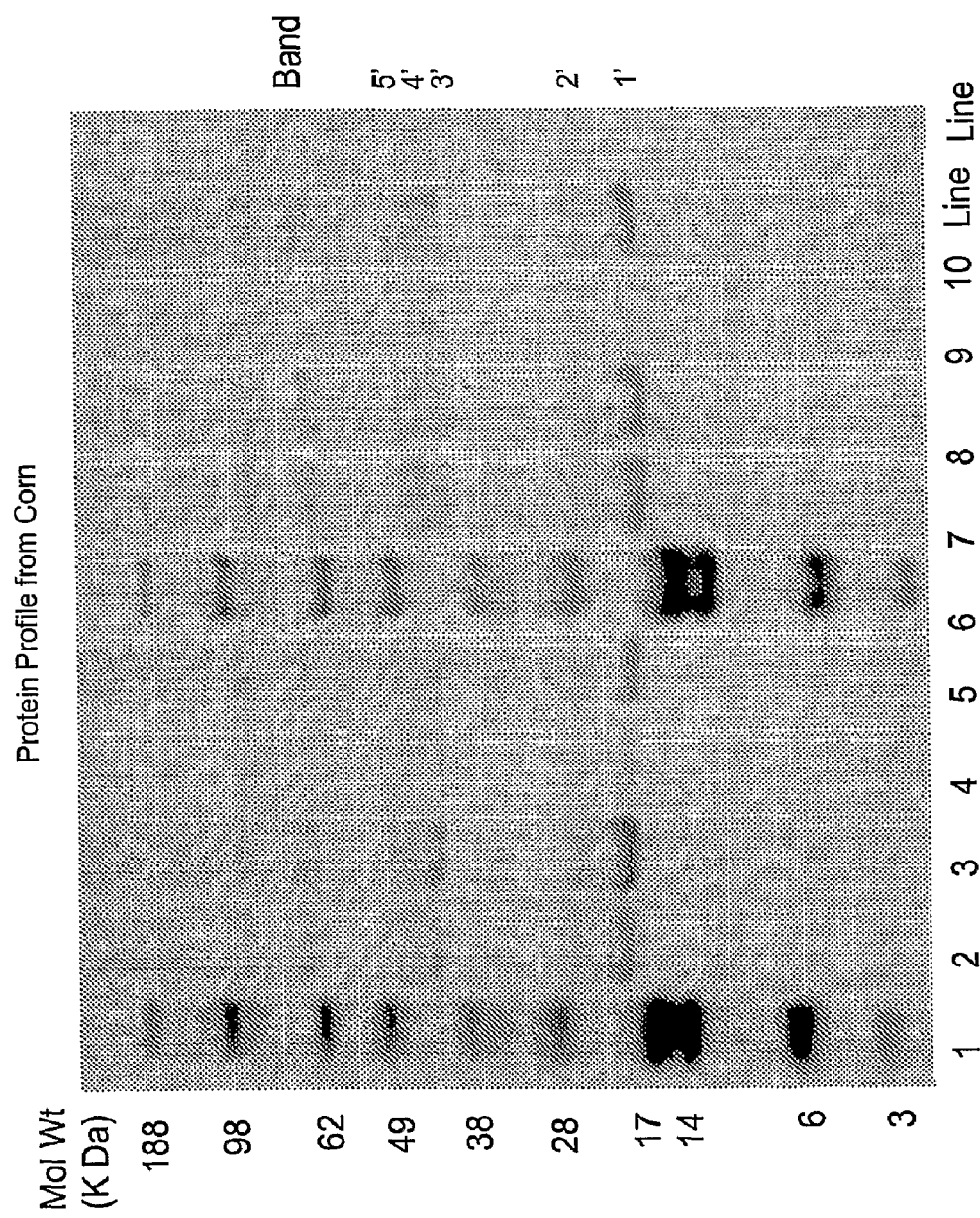
FIG. 7 illustrates the results of SDS-PAGE of the protein extracts from various corn samples (Lanes 1 and 6, molecular weight standards; Lanes 2 and 7, uncontaminated, ozonated corn; Lanes 3 and 8, uncontaminated, non-ozonated corn; Lanes 4 and 9, contaminated, ozonated corn; and Lanes 5 and 10, contaminated, non-ozonated corn).

FIG. 7 shows the results of SDS-PAGE analysis on the proteins extracted from the various corn samples. There were no differences in band pattern among the corn samples, indicating no differences in types of proteins. Differences in density of stain that could indicate concentration differences were not measured, but only visually inspected. For example, the lightest bands are found in Lanes 4 and 9, which correspond to the lowest measured % protein in the contaminated corn treated with ozonation (Table 4).

Example 4

Antimutagenicity of Lutein

Figure 8:
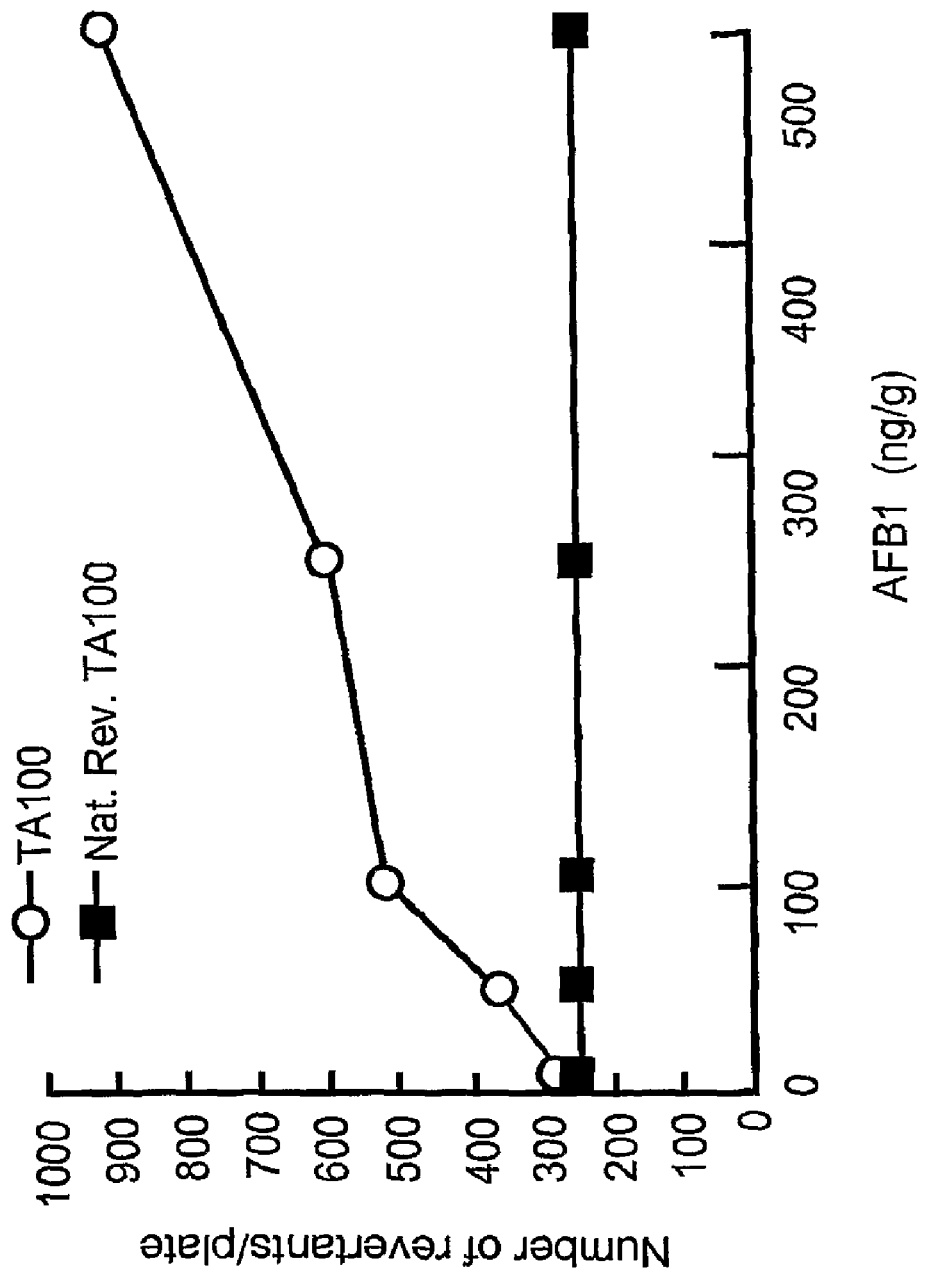
FIG. 8 illustrates a standard curve for mutagenic effect caused by increasing concentrations of aflatoxin B1 using an Ames test with *Salmonella typhimurium* tester strain TA100 with metabolic activation from Aroclor 1254-induced rat liver (S9).

The antimutagenic potential of lutein extracted from corn was evaluated to determine whether the ozonation process affected this known property of lutein. FIG. 8 illustrates a typical mutagenicity dose response curve for the effect of various concentrations of pure aflatoxin B1 (AFB1) on the mutagenic rate of the *Salmonella typhimurium* tester strain TA100, using an S9 mixture to help transform the AFB1 to the reactive metabolite. Values shown are the means of three replicates. As shown in FIG. 8, a concentration of 500 ng AFB1/plate had a mutagenic potency of about 925 revertants/plate. This curve was used below to predict an expected level of mutagenicity for AFB1.

Lutein standard and lutein extracts were investigated for their mutagenic potential. The results are shown below in Tables 5 and 6.

TABLE 5

Effect of Lutein Standard on Natural Mutagenicity

| Concentration of Lutein Standard (µg/plate) | Number of Revertants (without use of AFB1) |
|---|---|
| 0 | 251 ± 11 |
| 0.02 | 247 ± 15 |
| 0.2 | 258 ± 10 |
| 0.8 | 261 ± 13 |
| 2 | 243 ± 8 |
| 10 | 264 ± 12 |

TABLE 6

Effect of Corn Lutein Extracts on Mutagenicity

| | Number of Revertants (without use of AFB1) | | |
|---|---|---|---|
| Source of Lutein Extract | First Dilution (Lutein, µg/plate) | Second Dilution (Lutein, µg/plate) | Third Dilution (Lutein, µg/plate) |
| Clean corn with ozonation | 249 ± 7 (5.70) | 254 ± 12 (1.14) | 249 ± 9 (0.23) |
| Clean corn without ozonation | 262 ± 13 (4.50) | 257 ± 12 (0.90) | 243 ± 19 (0.18) |
| Contaminated corn with ozonation | 248 ± 14 (2.30) | 247 ± 11 (0.46) | 262 ± 11 (0.092) |
| Contaminated corn without ozonation | 243 ± 17 (3.2) | 258 ± 8 (0.64) | 249 ± 10 (0.128) |

As shown in Table 5, the number of revertants for lutein standard at concentrations of 0.2, 0.8, and 10 µg/plate were 254, 261, and 264, respectively. These are very close to the control (0 µg/plate) which was 251 (the natural number of revertants). In addition, as shown in Table 6, the corn lutein extracts at all dilutions produced a number of revertants similar to the control number. Therefore, the results from this Ames test indicated that neither purified lutein nor corn lutein extracts increase the number of revertants over the natural rate in TA100. These findings are consistent with a number of previous studies that demonstrated the absence of a mutagenic effect of lutein in *S. triphimurium* strains (Gonzalez de Mejia et al., 1997; and Rauscher et al., 1998). In addition, our results indicate that ozonation of the corn lutein extracts did not cause the lutein to now exhibit a mutagenic effect.

Figure 9:
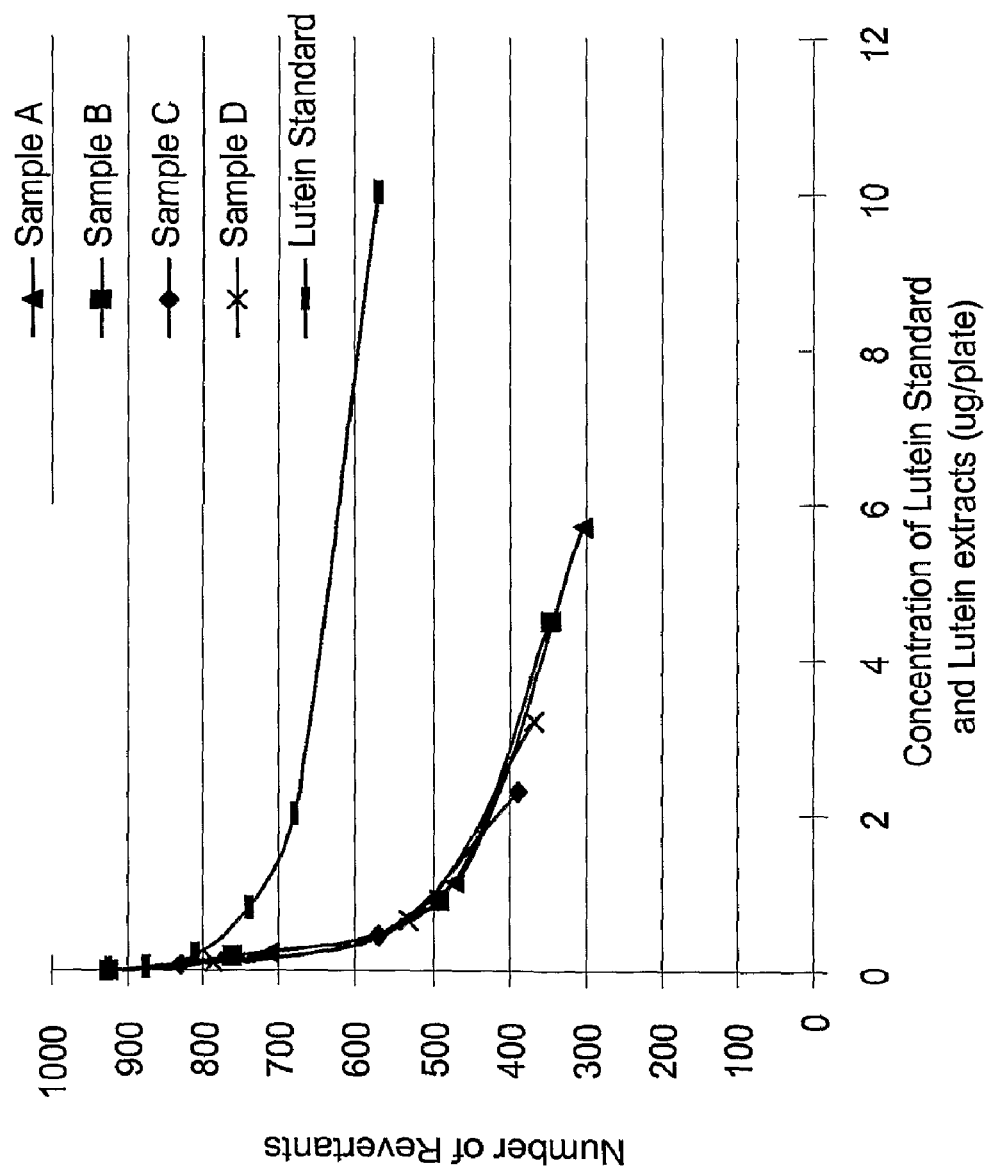
FIG. 9 illustrates the antimutagenic effect of various concentrations of a lutein standard and corn lutein extracts (A, uncontaminated, ozonated corn; B, uncontaminated, non-ozonated corn; C, contaminated, ozonated corn; and D, contaminated, non-ozonated corn) against the mutagenic activity of aflatoxin B1 (500 ng/plate), as shown using an Ames test with *Salmonella typhimurium* tester strain TA100 with metabolic activation from Aroclor 1254-induced rat liver (S9).

A dose of 500 ng AFB1/plate was chosen to investigate the antimutagenic activity of lutein. A standard curve of increasing concentrations of AFB1 and mutagenic effects is shown in FIG. 8. The antimutagenic effect of lutein standard and lutein extracts on AFB1 mutagenicity is shown in FIG. 9, and the results are summarized in Tables 7 and 8.

TABLE 7

Antimutagenic Potency of Lutein Standard Against AFB1 (500 ng/plate) in TA100 Stain

| Concentration (µg/plate) | Number of Revertants | Percent Inhibition (%) |
|---|---|---|
| 0 | 925 ± 23 | |
| 0.02 | 876 ± 34 | 5.3 |
| 0.2 | 813 ± 45 | 12.1 |
| 0.8 | 741 ± 25 | 19.9 |

TABLE 7-continued

Antimutagenic Potency of Lutein Standard
Against AFB1 (500 ng/plate) in TA100 Stain

| Concentration (μg/plate) | Number of Revertants | Percent Inhibition (%) |
|---|---|---|
| 2 | 679 ± 39 | 26.6 |
| 10 | 568 ± 50 | 38.6 |

TABLE 8

Antimutagenic Potency Number of Lutein Extracts
Against AFB1 (500 ng/plate) in TA100 Strain

| Source of Lutein Extract | Number of Revertants (With 500 ng/plate AFB1) (Percent Inhibition %) (Lutein μg/plate) | | |
|---|---|---|---|
| | First Dilution | Second Dilution | Third Dilution |
| Clean corn with ozonation | 302 ± 13 (67.4%) (5.70 μg/plate) | 470 ± 7 (49.2%) (1.14 μg/plate) | 713 ± 12 (22.9%) (0.23 μg/plate) |
| Clean corn without ozonation | 346 ± 20 (62.6%) (4.50 μg/plate) | 492 ± 4 (46.8%) (0.90 μg/plate) | 762 ± 21 (17.6%) (0.18 μg/plate) |
| Contaminated corn with ozonation | 389 ± 10 (57.9%) (2.30 μg/plate) | 571 ± 14 (38.3%) (0.46 μg/plate) | 830 ± 9 (10.3%) (0.092 μg/plate) |
| Contaminated corn without ozonation | 367 ± 11 (60.3%) (3.2 μg/plate) | 532 ± 20 (42.5%) (0.64 μg/plate) | 785 ± 13 (15.1%) (0.128 μg/plate) |

As shown in FIG. 9 and Tables 7 and 8, both the lutein standard and lutein extracts inhibited AFB1 (500 ng/plate) mutagenicity in a dose-response manner. All lutein extracts from corn were more effective at similar concentration than was the pure lutein standard, as shown in FIG. 9. All corn lutein extracts appeared to follow the same curve, indicating a similar degree of effectiveness at similar concentrations. These results suggest that the lutein extracts may contain other antimutagenic agents, and are thus more effective than pure lutein. This agrees with the literature. (Gonzalez de Mejia et al. (1997). Statistical analysis showed that the number of revertants when using AFB1 and lutein standard was significantly higher than that using lutein extracts (P≦0.001). Lutein extracts from the different corn samples had a similar antimutagenic potential. These results indicate that ozone did not affect the antimutagenic activity of lutein.

Example 5

Extraction of Lutein from Alfalfa

A bale of alfalfa was purchased in central Illinois from late harvest. For each ozonated sample, 500 gm alfalfa from the bale were cut into about 3 inch pieces and transferred to a 5 gallon plastic carboy container. Ozone gas was flowed in through the bottom of the container, through the sample, and exited the top. The samples were treated with 15 wt % ozone at a flow rate of 150 ml/min for time periods of 1 hr, 12 hr, and 72 hr (with mixing every 12 hr). After the ozone treatment, the samples were ground with a blender and milled using a Retsch centrifugal mill (Retsch, Inc., Newton, Pa.) with 1.0 mesh sieve. A control of 500 gm alfalfa was also cut into pieces, ground and then milled. Both the ozonated and control samples were further milled to pass through a 0.5 mesh sieve. The samples were then divided into three replicates for extraction of lutein.

Extraction and analysis of lutein was as discussed above in Example 1. In the samples that were ozonated for 12 hr and 72 hr, the extracted lutein showed signs of degradation. It is believed that ozonating for this length of time degraded the lutein in alfalfa. However, the lutein from the 1 hr ozonation was found not to be degraded.

In the first trial run at 1 hr, the ozonated samples had a higher lutein concentration than the control samples, 46.76 ppm and 43.58 ppm, respectively. These lutein values represent averages of the triplicate samples for the treated and untreated alfalfa. This indicated, about a 7% increase in extracted lutein concentration from the ozonated samples over the control.

Two additional samples were later taken from the same bale, ozonated, and analyzed for lutein. Unfortunately, control samples were not tested in these two runs. The lutein concentration from these two trials was substantially less than the original samples even after an additional hexane extraction, 32.4 ppm and 39.4 ppm. It is believe that these results indicated batch-to-batch differences in lutein found in the alfalfa bale.

A fourth trial was run on two additional batches from the alfalfa bale, one batch with treatment with ozone and the second for a control. For this trial, the lutein concentration was similar in both the ozonated and untreated samples, 31.7 ppm and 31.46 ppm, respectively. It is believed that this lowered lutein extraction reflected a difference in the starting alfalfa.

In the alfalfa that indicated the highest lutein concentration, ozonation increased the amount of lutein extracted. It is believed that the alfalfa sample with the highest lutein had more bound lutein that was released by the ozonation.

REFERENCES

Antony, J. I. X. and M. L. Shankaranarayana, 2001. The World of Food Ingredients. April/May 64-67.

Bewley, J. D.; Black, M. Structure of seeds and their food reserves. In Physiology and Biochemistry of Seeds in Relation to Germination, Vol. 1 Development, Germination and Growth; Spinger-Verlag: Berlin, 1978; Chapter 2, pp 7-37.

Dollear, F. G., G. E. Man, L. P. Codifer, H. K. Gardner, S. P. Koltun, and H. L. E. Vix. 1968. Elimination of aflatoxins from peanut meal. J. Am. Oil Chem. Soc. 45: 862-865.

Dwarakanath, C. T., E. T. Rayner, G. E. Man, and F. G. Dollear. 1968. Reduction of aflatoxin levels in cottonseed and peanut meals by ozonization. J. Am. Oil Chem. Soc. 45: 93-95.

Food and Agricultural Organization (FAO), 1998. World corn production. FAOSt database, Food and Agricultural Organization, Rome, Italy.

Gonzalez de Mejia, E., M. Ramos-Gomez, G. Loarca-Pina, 1997. Antimutagenic activity of natural xanthophylls against Aflatoxin B1 in *Salmonella typhimurium*. Environmental and Molecular Mutagenic. 30: 346-353.

Gonzalez de Mejia, G. Loarca-Pina, E., M. Ramos-Gomez, 1997. Antimutagenicity of xanthophylls present in Aztec Marigold (*Tagetes erecta*) against 1-nitropyrene. Mutation Res. 389: 219-226.

Huck, C. W., Popp, M., Scherz, H., and Bonn, G. K. 2000. Development and evaluation of a new method for the determination of the carotenoid content in selected vegetables by HPLC and HPLC-MS-MS. J. Chromatogr. Sci. (38), 441-449.

Lakshminarayana R, Raju M, Krishnakantha T P, Baskaran V. (2005). Determination of major carotenoids in a few Indian leafy vegetables by high-performance liquid chromatography. J Agric Food Chem. 53(8):2838-2842.

Li, H. B., Jiang, Y., and Chen, F. 2002. Isolation and Purification of lutein from the microalga *Chlorella vulgaris* by Extraction after Saponification. J. Agric. Food Chem 50:1070-1072.

Maron, D. M. and B. N. Ames. 1983. Revised methods for the *Salmonella* mutagenicity test. Mutation Res. 113: 173-215.

McKenzie, K. S. 1997. Degradation and detoxification of common chemical contaminants of food ad water using ozone generated by electrolysis. A Ph.D. Dissertation, Texas A&M University. pp 200.

McKenzie, K. S., L. F. Kubena, A. J. Dencir, T. D. Rogers, G. D. Hitchens, R. H. Bailey, R. b. Harvey, S. A. Buckley, and T. D. Philips. 1998. Aflatoxicosis in turkey poults is prevented by treatment of naturally contaminated corn with ozone generated by electrolysis. Poultry Science. 77:1094-1102.

Moros, E. E., D. Darnoko, M. Cheryan, E. G. Perkins, and J. Jerrell. 2002. Analysis of Xanthophylls in Corn by HPLC. J. Argic. Food. Chem. 50: 5787-5790.

Norton, R. A. 1997. Effects of carotenoids on aflatoxins synthesis by *Aspergillus falvus*. Phytopathology. 87(8): 815-821.

Park, K. Y., Jung G. O., Lee K. T., Choi, J., Choi, M. Y., Kim, G. T., Jung, H. J., and Park, H. J. 2004. Antimutagenic activity of flavonoids from the heartwood of *Rhus verniciflua*. Journal of Ethnopharmacology 90:73-79.

Prudente, A. D. (2001) Efficacy and Safety Evaluation of Ozonation To Degrade Aflatoxin in Corn. A Master Thesis, Louisiana State University Prudente, A. D. and King, J. M 2002 *Efficacy and Safety Evaluation of Ozonation to Degrade Aflatoxin in Corn*. Journal of Food Science. 67:2866-2872.

Rauscher, R., R. Edenharder, and K. L. Platt. 1998. In virto antimutagenic and in vivo anticlastogenic effects of carotenoids and solvent extracts from fruits and vegetables rich in carotenoids. Mutation Res. 413: 129-142.

Rooney, L. W. and S. O, Serna-Salvador. 1987. Food uses of whole corn and dry-milled fractions. In: Corn Chemistry and technology. Watson, S. A. and Ramsted, R. E. (Eds). Am. Assoc. Cereal Chemists. St. Paul, Minn. p. 399-429.

Samarajeewa, U., A. C. Sen, M. D. Cohen, and C. T. Wei. 1990. Detoxification of aflatoxins in foods and feeds by physical and chemical methods. J. Food Protect. 53(6): 489-501.

Slattery M L, Sorenson A W, Mahoney A W, French T K, Kritchevsky D, Street J C. 1988. Diet and colon cancer: assessment of risk by fiber type and food source. J Natl Cancer inst. 80(18): 1474-1480.

The complete disclosures of all references cited in this application are hereby incorporated by reference. Also, incorporated by reference is the complete disclosure of the following documents: Yu Wang, "Evaluation of Lutein and Protein in Ozone Treated Corn," A thesis submitted to the Department of Food Science, Louisiana State University, August, 2005; and Y. Wang et al., "Evaluation of Lutein and Protein in Ozone-Treated Corn," An abstract for the 2005 Annual Meeting of the Institute of Food Technologists, published online March 2005. In the event of an otherwise irreconcilable conflict, however, the present specification shall control.

What is claimed:

1. A process for extracting lutein from a plant source containing free and bound lutein, said process comprising the consecutive steps of:
    (a) Exposing the plant source to ozone in a concentration for a time sufficient to release bound lutein but insufficient to substantially degrade the lutein;
    (b) Grinding the plant source;
    (c) Treating the ground plant source with a base in a concentration and for a time sufficient to saponify the mixture;
    (d) Cooling the saponified mixture below ambient temperature;
    (e) Adding a nonpolar solvent to the saponifed mixture at a sufficiently low temperature and for a sufficiently long time to dissolve most of the lutein into the nonpolar solvent;
    (f) Collecting the solution with dissolved lutein; and
    (g) Evaporating the solvent to leave a residue of lutein.

2. A method as in claim 1, wherein said plant lutein source is selected from the group consisting of corn, marigold, alfalfa, broccoli, kale, carrot, spinach, and other green leafy vegetables.

3. A method as in claim 1, wherein the plant lutein source is corn.

4. A method as in claim 3, wherein the corn is not contaminated with aflatoxin.

5. A method as in claim 3, wherein the corn is contaminated with aflatoxin.

6. A method as in claim 3, wherein time of ozone treatment is about 96 hr.

7. A method as in claim 1, wherein the plant lutein source is alfalfa.

8. A method as in claim 7, wherein the time of ozone treatment is less than about 12 hr.

9. A method as in claim 8, wherein the time of ozone treatment is about 1 hr.

10. A method as in claim 1, wherein the nonpolar solvent is hexane.

11. A method to increase the amount of free, undegraded lutein that can be extracted from a plant source containing both free and bound lutein, said method comprising first exposing the plant source to ozone for a time sufficient to release the bound lutein but insufficient to substantially degrade the lutein, and second extracting the lutein from the plant source.

12. A method as in claim 11, wherein said plant source is selected from the group consisting of corn, marigold, alfalfa, broccoli, kale, carrot, spinach, and other green leafy vegetables.

13. A method as in claim 11, wherein the plant source is corn.

14. A method as in claim 13, wherein the time of ozone treatment is about 96 hr.

15. A method as in claim 11, wherein the plant source is alfalfa.

16. A method as in claim 15, wherein the time of ozone treatment is less than abut 12 hr.

17. A method as in claim 15, wherein the time of ozone treatment is about 1 hr.

* * * * *